(12) United States Patent
Bou Aoun et al.

(10) Patent No.: US 10,814,285 B2
(45) Date of Patent: Oct. 27, 2020

(54) FUNCTIONALIZED MEMBRANES FOR BIOARTIFICIAL ORGANS

(71) Applicant: Defymed, Strasbourg (FR)

(72) Inventors: Richard Bou Aoun, Strasbourg (FR); Charles-Thibault Burcez, Strasbourg (FR); Jordan Magisson, Strasbourg (FR); Séverine Sigrist, Strasbourg (FR)

(73) Assignee: Defymed, Strasbourg (FR)

( * ) Notice: Subject to any disclaimer, the term of this patent is extended or adjusted under 35 U.S.C. 154(b) by 102 days.

(21) Appl. No.: 15/575,015

(22) PCT Filed: May 17, 2016

(86) PCT No.: PCT/EP2016/061051
§ 371 (c)(1),
(2) Date: Nov. 17, 2017

(87) PCT Pub. No.: WO2016/184872
PCT Pub. Date: Nov. 24, 2016

(65) Prior Publication Data
US 2018/0147543 A1  May 31, 2018

(30) Foreign Application Priority Data
May 18, 2015 (EP) .................................. 15305741

(51) Int. Cl.
*B01D 67/00* (2006.01)
*A61L 33/00* (2006.01)
(Continued)

(52) U.S. Cl.
CPC .......... *B01D 67/0088* (2013.01); *A61L 27/26* (2013.01); *A61L 27/34* (2013.01);
(Continued)

(58) Field of Classification Search
CPC .... B01D 67/0088; B01D 69/02; B01D 69/12; B01D 71/08; B01D 69/105;
(Continued)

(56) References Cited

U.S. PATENT DOCUMENTS 5,152,894 A * 10/1992 Haubs .................... B01D 71/56
                                                          210/500.38
5,401,410 A *  3/1995 Bell ..................... B01D 67/0011
                                                          210/490
(Continued)

FOREIGN PATENT DOCUMENTS

EP      0 086 186       5/1986
EP      0 658 112       7/2001
(Continued)

OTHER PUBLICATIONS

Gümüşdereliŏglu et al., *Heparin-functionalized chitosan scaffolds for bone tissue engineering*, 346 Carbohydrate Research 606-613 (2011).
(Continued)

*Primary Examiner* — Aradhana Sasan
*Assistant Examiner* — Quanglong N Truong
(74) *Attorney, Agent, or Firm* — Panitch Schwarze Belisario & Nadel LLP

(57) ABSTRACT

The invention relates to a heparin-functionalized semi-permeable membrane comprising at least one layer of porous biocompatible polymer, and one layer of non-woven biocompatible polymer wherein said heparin is covalently bound to a layer on the surface of said porous biocompatible polymer.

15 Claims, 8 Drawing Sheets

(51) Int. Cl.
| | |
|---|---|
| B01D 69/10 | (2006.01) |
| A61L 27/26 | (2006.01) |
| A61L 27/34 | (2006.01) |
| A61L 27/54 | (2006.01) |
| A61L 27/56 | (2006.01) |
| A61L 33/08 | (2006.01) |
| B01D 69/02 | (2006.01) |
| B01D 69/12 | (2006.01) |
| B01D 71/08 | (2006.01) |

(52) U.S. Cl.
CPC ............... *A61L 27/54* (2013.01); *A61L 27/56* (2013.01); *A61L 33/0011* (2013.01); *A61L 33/08* (2013.01); *B01D 69/02* (2013.01); *B01D 69/105* (2013.01); *B01D 69/12* (2013.01); *B01D 71/08* (2013.01); *A61L 2300/236* (2013.01); *A61L 2300/42* (2013.01); *A61L 2400/18* (2013.01); *B01D 2323/36* (2013.01); *B01D 2325/04* (2013.01)

(58) Field of Classification Search
CPC . B01D 2323/36; B01D 2325/04; A61L 27/34; A61L 33/08; A61L 27/56; A61L 27/26; A61L 27/54; A61L 33/0011; A61L 2300/42; A61L 2300/236; A61L 2400/18
See application file for complete search history.

(56) References Cited

U.S. PATENT DOCUMENTS

| | | | | |
|---|---|---|---|---|
| 5,403,750 A | * | 4/1995 | Braatz | A61L 27/34 210/500.24 |
| 10,022,404 B2 | * | 7/2018 | Bou Aoun | A61K 38/28 |
| 2003/0021826 A1 | | 1/2003 | Crost et al. | |
| 2007/0118210 A1 | * | 5/2007 | Pinchuk | A61F 2/2412 623/1.26 |
| 2011/0064781 A1 | | 3/2011 | Cleek et al. | |
| 2012/0231043 A1 | | 9/2012 | Leontein et al. | |
| 2013/0131828 A1 | | 5/2013 | Legeay et al. | |
| 2014/0242710 A1 | | 8/2014 | Suri et al. | |

FOREIGN PATENT DOCUMENTS

| | | |
|---|---|---|
| EP | 1 112 098 | 2/2003 |
| EP | 1 112 097 | 6/2003 |
| WO | WO 93/05793 | 4/1993 |
| WO | WO 2006/080009 | 8/2006 |

OTHER PUBLICATIONS

Johnell et al., *Coagulation, fibrinolysis, and cell activation in patients and shed mediastinal blood during coronary artery bypass grafting with a new heparin-coated surface*, 124(2) The Journal of Thoracic and Cardiovascular Surgery 321-332 (Aug. 2002).

Kristensen et al., *Characterization of heparin surfaces using photoelectron spectroscopy and quartz crystal microbalance*, 24 Biomaterials 4153-4159 (2003).

Kristensen et al., *Heparin coating durability on artificial heart valves studied by XPS and antithrombin binding capacity*, 49 Colloids and Surfaces B: Biointerfaces 1-7 (2006).

Leijon et al., *Attachment of Flexible Heparin Chains to Gelatin Scaffolds Improves Endothelial Cell Infiltration*, 19 (11 and 12) Tissue Engineering; Part A (2013).

Murugesan et al., *Immobilization of Heparin: Approaches and Applications*, 8 Current Topics in Medicinal Chemistry 80-100 (2008).

International Search report dated Jul. 20, 2016, in corresponding International Application PCT/EP2016/061051.

* cited by examiner

FUNCTIONALIZED MEMBRANES FOR BIOARTIFICIAL ORGANS

CROSS-REFERENCE TO RELATED APPLICATIONS

This application is a U.S. National Stage Application pursuant to 35 U.S.C. § 371 of International Patent Application PCT/EP2016/061051, filed on May 17, 2016, and published as WO 2016/184872 on Nov. 24, 2016, which claims priority to European Patent Application 15305741.9, filed on May 18, 2015, all of which are incorporated herein by reference in their entireties for all purposes.

The invention relates to the field of implantable bioartificial organs made of biocompatible membranes, and in particular of semi-permeables membranes, that allow cells to secrete a substance of interest out of the organ, without making it possible for unwanted substances (such as substances from the immune system) to enter the organ.

The treatment of pathological conditions requiring a continuous supply, to the body, of substances of therapeutic interest has made necessary the development of devices which can be implanted in a patient and are capable of releasing these substances efficiently and sometimes for long periods of time.

To satisfy this need, bioartificial organs which contain cells producing one or more substances of therapeutic interest have been developed. The cells contained in a bioartificial organ are confined in internal spaces, or encapsulating chambers, delimited by at least one semi-permeable membrane. Such a membrane is termed "semi-permeable" when it allows the diffusion of the substances of therapeutic interest out of the encapsulating chamber to the target cells in the patient's body, while at the same time being impermeable to the antibodies and the cells of the patient's immune system, thus preventing them from directly attaching the cells producing the substance(s) of therapeutic interest.

A bioartificial organ is understood to be a device, in particular intended to be implanted in a patient, comprising at least one encapsulating chamber consisting of at least one semi-permeable membrane; said encapsulating chamber is intended to contain cells which secrete one or more substance(s) of therapeutic interest.

These substances of therapeutic interest are any substance intended to have a beneficial effect in the patient. These may therefore be a neurotransmitter, a hormone, a growth factor, a coagulation factor or a cytokine. In particular, these substances may be, without any limiting nature, insulin, glucagon, growth hormone, coagulation factor IX, coagulation cofactor VIII or calcitonin.

Examples of devices (bioartificial organs, semi-permeable membranes, encapsulating chambers) are known in the prior art.

Mention may thus be made of WO 02/060409 which describes a membrane consisting of a porous polycarbonate biocompatible film which is surface-modified by generation of polar sites and covered with a layer of at least one hydrophilic polymer, and the use thereof for manufacturing bioartificial organs.

WO 2012/017337, US 2013/131828 and FR 2960783 describe a functionalized semi-permeable membrane composed of a porous biocompatible support pretreated so as to increase the surface energy thereof and comprising at least two layers, each comprising a hydrophilic polymer and at least one biologically active molecule, and also the use thereof in particular for manufacturing a bioartificial organ and an encapsulation chamber. The biologically active molecules disclosed in this application are VEGF and heparin, which is, in particular, present in a HPMC or EC layer. These membranes don't possess the layer of a non-woven polymer.

WO 2012/010767 describes a bag (or pouch or pocket) for forming an implantable artificial organ, which comprises a closed shell made of a semi-permeable membrane. This bag also comprises a sheet contained in the shell, the sheet comprising projections (protuberances) on the surface thereof for maintaining a space for cells between the sheet and the shell.

PCT/EP2014/076955 (WO 2015/086550) describes a chamber for encapsulating secreting cells producing at least one substance of therapeutic interest, comprising a closed shell made of a semi-permeable membrane, delimiting a space capable of containing said secreting cells producing at least one substance of therapeutic interest, wherein said membrane comprises at least one layer of porous biocompatible polymer, and one layer of non-woven biocompatible polymer. This application discloses the functionalization of the membrane with heparin that is contained in a hydrophilic layer of HPMC or ethylcellulose.

WO 2006/080009 discloses an implantable device chamber for encapsulating secreting cells, the chamber(s) being encapsulated by a membrane made of non-woven electrospun fibres and being further impregnated with heparin.

However, the membrane of WO 2006/080009 doesn't comprise a layer of a porous biocompatible polymer layer (P) and a layer of a nonwoven biopolymer layer (NW), which are distinct layers, as indicated below and on FIG. 8.

Furthermore, the membrane of WO 2006/080009 is impregnated with heparin, and there is thus a risk of a release of heparin after implantation, since a simple impregnation doesn't guarantee a stable attachment of heparin on membrane. WO 2006/080009 is silent about this problem, which has been identified by the Applicant, as indicated below.

US 2003/021826 discloses a composite membrane for blood treatment wherein porous support is treated with a cationic polymer in order to bind heparin to the surface.

Gumusderelioglu and Aday (Carbohydrate Research, vol. 346, no. 5, 8 Dec. 2010, pages 606-613) disclose Heparin-functionalized chitosan scaffolds for bone tissue engineering, US 2012/231043 discloses a method to covalently bind conjugates of dendrimers carrying a high number of heparin groups via amino groups of the dendrimer molecule to a surface to be modified also via remaining primary amino groups. The method is applied for implants WO 93/05793 discloses to form a conjugate of a carrier polymer and at least 20 heparin groups connected via amino groups and binding it via ionic bonds to the surface of a substrate to render it biocompatible.

US 20110064781 discloses immobilized biologically active entities retaining biological activity following manipulation, and in particular a medical substrate comprising a heparin entity bound onto a substrate via at least one heparin molecule.

Heparin occurs naturally complex-bound to protein in various mammalian tissues and has a molecular weight which may extend up to 100,000 (commercially available heparins have a molecular weight varying between about 6,000 and 20,000 depending on the source and the determination method.)

Heparin consists of alternating glucuronic acid and glucosamine units, and the anti-coagulating effect has been shown to be linked to a specific pentasaccharide unit of the molecule which has antithrombin-binding properties and anti-inflammatory properties, depending on its concentration. It is thus important for this unit to be available in order to observe the effects of heparin.

In the above patent applications, the membranes and bioartificial organs are described as possibly functionalized with heparin. The heparin is contained in a layer of a hydrophilic polymer, in free form.

The applicant noticed that there is thus a risk of a burst release of heparin upon implantation (release of heparin within the body of the host and decrease of the local heparin quantity) which would lower the biological efficiency of the heparin (anti-inflammatory effect, as well as improving local vascularization of the device, needed to permit survival of the cells contained within the bioartificial organ).

Furthermore, the applicant noticed that it is difficult to measure the quantity of heparin that is present at the surface of the device, probably due to the presence of the layer of hydrophilic polymer. This may prove to be problematic from a regulatory point of view.

Last, the biological effect of heparin may not be as potentiated as it could be, as the antithrombin pentasaccharide unit of the molecule may not be sufficiently available.

It is thus necessary to provide other bioartificial organs presenting heparin at their surfaces, so that the heparin can be easily quantified, and so that there is no (or marginal) loss of heparin after implantation.

The applicant thus propose to provide novel membranes the surface of which presents heparin, in such a way to reduce the risk that heparin is easily released in the circulation after implantation of the organ made with said membranes.

The solution proposed by the application is to use technologies where the heparin is covalently bound to a support or polymer.

Said support may be
  a polymer that was applied to the surface of the membrane. This technology may also be qualified as coupling by end point attachment of the heparin, and is described in particular in EP 1112097 and EP 1112098 or in LaFrance and Dapron (J Mol Recognit. 1996; 9(5-6):748-51).
  or
  a substantially straight-chained organic polymer, the heparinized polymer being then applied to the surface of the membrane. Said technology is described in particular in EP 658112 or in Van der Giessen et al (Curr. Intervent. Cardiol. Rep. 1 (1999) 234) or in Kristensen et al (Biomaterials 24 (2003) 4153). In this technology, heparin is also attached at its end to the polymer, and it remains irreversibly attached to the membrane surface by means of multiple ionic interactions.

Other methods such as the ones described in Murugesan et al (Curr Top Med Chem. 2008; 8(2):80-100) can also be used.

The examples show that the membranes and method described in the present application makes it possible to obtain membranes that present the same semi-permeability than the ones of the prior art, and that possess superior in vivo properties as attested by reduction of fibrosis after implantation in rats and increase in vessel size or numbers that would probably reflect better vascularization. Furthermore, the membranes obtained by the methods described herein would probably be more compliant with regulatory concerns for devices made with the membrane as allowing analysis of the heparin at the surface of the membrane. Last, there is excellent stability of the heparin at the surface of the membrane overtime.

The invention thus relates to a heparin-functionalized biocompatible semi-permeable membrane, wherein said membrane comprises at least one layer of porous biocompatible polymer, and one layer of non-woven biocompatible polymer and wherein said heparin is covalently bound to a layer on the surface of said porous biocompatible polymer.

Preferably, heparin is attached to the layer through end point attachment, i.e. the end of the heparin molecule is attached to a reactive site of the layer, thereby leaving unrestricted access to the sequences required for biospecific interaction within the heparin polysaccharide chain.

In any case, it is to be noted that the heparin is not directly bound to the surface of said porous biocompatible polymer, but is bound to a "priming" layer that has first applied to said surface in order to "activate" or "prime" the surface and allow the irreversible binding of heparin to this priming layer (either through covalent or strong ionic/electrostatic bounds). A main effect of the functionalized membrane herein described is that heparin is not in a free (i.e. not bound) form at the surface of the membrane, as it is when present in a hydrophilic polymer layer, and would thus likely present better stability and biological effects, as shown in the examples.

It is also to be noted that layer of various polymers may be applied to the surface of the membrane before the priming layer is deposited, for instance by the layer-by-layer technique.

It is recalled that the term "biocompatible" is said of a material which is well tolerated by a living organism and which does not cause a rejection reaction, a toxic reaction, a lesion or a harmful effect on the biological functions of the latter. This does not exclude the possibility of an inflammatory reaction due to the insertion of the material into the organism or of an immune reaction in the case of a biocompatible organ comprising exogenous cells; this immune reaction is not therefore due to the organ as such, but instead due to its content (secretion of chemokines by the exogenous cells).

The membrane is semi-permeable, indicating that it presents a cut-off threshold, the molecules having a weight above this cut-off threshold being unable to cross the membrane, while the molecules having a weight below this cut-off threshold can cross the membrane. The determination of the cut-off threshold is carried out by those skilled in the art according to the characteristics of the molecules that they wish to stop or allow to penetrate.

In one preferred embodiment, and in order to allow the passing of small molecules such as insulin, glucagon or glucose and to stop the effector molecules of the immune system (such as antibodies and complement factors), this cut-off threshold is between 40 kDa and 500 kDa, or between 100 kDa and 500 kDa, or between 100 kDa and 150 kDa, more preferably between 50 kDa and 150 kDa.

The internal diameter of the pores of the porous polymer makes it possible to obtain the desired cut-off threshold. Thus, in one particular case, the internal diameter of the pores present on the layer of porous biocompatible polymer is between 5 and 100 nm, entirely preferably between 5 and 50 nm.

In a preferred embodiment, said membrane comprises a layer of biocompatible non-woven polymer located between two layers of porous biocompatible polymers and wherein said layer of heparin is present on the surface of at least one layer of porous biocompatible polymer.

Said membranes are further described below.

Binding Heparin to a Straight-Chained Organic Polymer

As indicated above, in a specific embodiment, said heparin layer consists in a substantially straight-chained organic polymer having a number of functional groups distributed along the polymer backbone chain, via which groups at least 20 molecules of heparins are anchored through covalent bonds, wherein the heparins are bound to the polymer backbone chain via an amino group or amino acid associated with the heparins, and wherein said heparin layer is affinity bound to the surface of said layer of porous biocompatible polymer.

This method is actually disclosed in EP 658112.

Briefly, one uses an at least substantially water-soluble, biologically active conjugate (macromolecule), preferably in substantially pure form, comprising a substantially straight-chained organic homo- or heteropolymer having a number of functional groups distributed along the polymer backbone chain, via which groups of at least about 20 molecules of heparin are anchored through covalent bonds wherein heparin is bound to the polymer backbone chain via an amino group or amino acid associated with heparin. It could be noted that heparan sulphate, dermatan sulphate, chondroitin sulphate, but also fragments and derivatives of these substances which are functional for the purpose can be equivalently used and substituted to heparin. As indicated in EP 658112, the number of heparin residues per polymer backbone chain is, as mentioned above, at least 20, but preferably higher, usually at least 30. Depending on the polymer backbone chain used, it may be preferred to have at least 60 and even more than 100 heparin residues per polymer backbone chain. The upper limit depends on the circumstances and is set inter alia by the solubility properties of the selected carrier polymer, how high a viscosity that may be permitted, and the like.

The Substantially Linear Polymer

The substantially linear polymer chain is preferably substantially biologically inert after the coupling of heparin, i.e. devoid of interfering biological activity.

It should present a number of functional groups, such as amino, hydroxyl or carboxyl groups, distributed along the chain and capable of, after optional modification, being coupled to the heparin, either directly or via a coupling sequence.

The carrier polymer should preferably have a good solubility in water. At least it should, in accordance with what has previously been said about the conjugate, be at least substantially water-soluble after the coupling of heparin.

Specific and preferred polymer chains are natural or synthetic polypeptide, polysaccharide or aliphatic polymer, such as polylysine, polyornithine, chitosan, polyimine and polyallylamine.

Binding of the Conjugate Polymer/Heparin to the Membrane Surface

This conjugate is bound to the membrane surface, which may have been prepared to have affinity to the conjugate (usually but not necessarily to the heparin residues) so as to thereby provide the surface with the desired biological activity.

The functionalized membrane is obtained by simply contacting, under suitable conditions, the conjugate (comprising the organic polymer having a number of functional groups, via heparin molecules anchored by covalent bonds), with the membrane surface prepared to present affinity to the conjugate.

A preferred form of affinity between the conjugate and the substrate surface is of electrostatic nature, and more particularly that binding takes place by electrostatic interaction between the heparin residues and the membrane surface. Indeed, one will use the electrostatic net charge of the conjugate, which is sufficient to permit substantially irreversible binding to an oppositely charged membrane surface. Since the conjugate is negatively charged, the membrane surface shall be or shall be made cationic.

Various methods for making the membrane surface cationic are well known. Treatment with polyimine is a suitable method, but also other polyamines, such as polylysine, chitosan or polyallylamine, may be used. These polymers are used in the examples of EP 658112.

Coupling of Heparin to the Polymer

There are different ways to couple the heparin to the substantially straight-chained organic polymer.

It is however preferred that each heparin molecule is bound terminally and by only a single bond to the carrier polymer. Suitably, the heparin molecule is bound via an amino acid, and then preferably a terminal amino acid, but also free amino groups of a heparin unit may be used. The latter may exist free as such or may have been liberated through desulphation or deacetylation.

In particular, the heparin may be bound directly to an amino-functional polymer chain utilizing a nitrous acid degraded heparin having a terminally located aldehyde group prepared according to the method described in U.S. Pat. No. 4,613,665.

Preferably, the heparin is bound to the polymer chain by means of a coupling reagent, and preferably a heterobifunctional one, such as N-succinimidyl-3-(2-pyridyldithio)-propionate (SPDP).

As a way of illustration, coupling of heparin to a polylysine (having a molecular weight above 400,000) will be described to lead a conjugate having up to 500 heparin chains per carrier molecule may be prepared.

N-succinimidyl-3-(2-pyridyldithio)-propionate (SPDP), is coupled to amino groups on the polylysine, the SPDP-substituted polylysine then being purified chromatographically. In a separate coupling step, SPDP is also coupled to amino groups on heparin which are present either in terminal amino acid residues or as free glucosamine (the latter content may be controlled via N-desulphation or N-deacetylation). The SPDP-groups are reduced to thiol function, whereupon the SH-substituted heparin is purified chromatographically. The content of SPDP groups in polylysine and SH-groups in heparin, respectively, are determined spectrophotometrically, and heparin is mixed with polylysine in an equimolecular amount with regard to SPDP and SH, heparin being bound covalently to polylysine via disulphide exchange, the reaction rate of which may be followed spectrophotometrically. The precipitation reaction between polylysine and heparin does not take place when polylysine has been provided with SPDP-groups, even if only a certain portion of the amino groups of polylysine have been substituted. Practical experiments have shown that the disulphide exchange is quicker and proceeds to completion only at a high salt concentration (suitably 3 M NaCl). When the reaction is completed, the conjugate is purified chromatographically, free heparin and low-molecular reaction products being removed.

Binding Heparin by End-Point Attachment to the Layer

In another embodiment, said heparin layer consists in heparin molecules covalently bound to a layer of a polymer applied on the surface of said layer of porous biocompatible polymer.

Methods to perform such embodiment are disclosed in details in EP 86186, EP 1112097 and EP 1112098.

The membrane surface is primed by applying a polymeric base matrix using a layer-by-layer technique. As a matter of illustration, the preferred method is to use a cationic amino polymer to be adsorbed to the material surface, followed by an anionic polymer and a polymeric amine. Additional layers of anionic and cationic polymers may also be applied to achieve optimal functional characteristics and coverage of the underlying material.

The technology is based on a chemical modification of heparin (diazotization, usually performed in an aqueous solution with a suitable diazotizing agent, e.g. a nitrite, such as sodium nitrite, in acid solution or butyl nitrite) that results in formation of a reactive aldehyde group at one end of the linear molecule. These groups are then reacted with primary amino groups incorporated on the material surface by the priming procedure, leading to formation of Schiff's bases, which are then reduced with a suitable reducing agent, such as a cyanoborohydride, preferably of an alkali metal, such as sodium, potassium or lithium, to yield stable covalent bonds.

Description of the Membrane

Non-Woven Polymer

A non-woven polymer (non-woven) is such that the fibers thereof are maintained randomly. It is thus a sheet consisting of fibers oriented in a particular direction or randomly, bonded by friction and/or cohesion and/or adhesion. The fibers are thus arranged statistically, i.e. deposited randomly. Consequently and due to the random arrangement of the fibers, the non-woven polymer is permeable to substances, and there is no control of the size of the substances that can diffuse within the non-woven polymer. FIG. 8 shows that the non-woven membrane is not structured as the porous membranes and that there is no control of diffusion of substance within the non-woven part of the membrane, in contrast to porous membranes, which present a cut-off, depending on the size of pores, as described below.

Non-woven polymers can be produced using polymeric fibers of any type. Mention may thus be made of polyesters: PET (poly(ethylene terephthalate)), PBT (poly(butylene terephthalate)), PVC (poly(vinyl chloride)), PP (polypropylene), PE (polyethylene) or blends of these polymers.

Polyamides or polycarbonates can also be used to produce non-woven polymers.

Preferably, the non-woven polymer is chosen from polycarbonate (PC), polyester, polyethyleneimine, polypropylene (PP), poly(ethylene terephthalate) (PET), poly(vinyl chloride) (PVC), polyamide and polyethylene (PE). Blends of these polymers can also be used for producing the non-woven polymer. Poly(ethylene terephthalate) (PET) is particularly preferred.

Generally, this non-woven polymer is obtained by the meltblown method. The composition thereof is an entanglement of microfibres which have been "melt blown".

This method of production is particularly suitable for polymers which can be melt spun, in particular polypropylene, poly(ethylene terephthalate), polyamides or polyethylene.

This method generates non-wovens of greater mechanical strength.

In a particular embodiment, the membrane comprises two layers of porous biocompatible polymers, on either side of the layer of biocompatible non-woven polymer, as shown on FIG. 8. Thus, this layer of biocompatible non-woven polymer is located, positioned or situated between these two layers of porous biocompatible polymers.

Such an embodiment makes it possible to optimize the strength and resistance of the bioartificial organe. Indeed, this layer of non-woven can be considered to behave like a "sponge", which gives it the capacity to absorb impacts and to deform, thus increasing the rigidity of the membrane in situ, but which can prove to be troublesome in the presence of cells, which can have a tendency to form aggregates around this non-woven. Locating the layer of non-woven between two porous layers of biocompatible polymers thus makes it possible to prevent the aggregation of cells while at the same time providing the device with additional protection/strength, and with no effect on the molecular diffusion of the biological substances.

It is not necessary for the porous and non-woven biopolymers to be identical.

Likewise, in the presence of two layers of porous biopolymers, the latter can be the same polymer or different polymers.

When the membrane presents two layers of porous biopolymers, it is possible to functionalize only one of them with heparin. Alternatively, both layers of porous biopolymers are functionalized with heparin.

Porous Biocompatible Polymer

The porous biocompatible polymer consists of a polymer known in the art. Thus, it may be chosen from polycarbonate (PC), polyester, polyethyleneimine, polypropylene (PP), poly(ethylene terephthalate) (PET), poly(vinyl chloride) (PVC), polyamide and polyethylene (PE).

In one particular embodiment, at least one layer or the two layers, as appropriate, is (are) made of poly(ethylene terephthalate) (PET).

The pore formation is carried out by any method known in the art. In particular, it is possible to use the electron bombardment method or the heavy ion bombardment method (this second technique is in particular described in U.S. Pat. No. 4,956,219). In the case of heavy ion bombardment, the density of the heavy ions bombarded at the surface of the biocompatible support determines the pore density, while the chemical erosion treatment time determines the pore size.

The membranes are thus prepared using the "track-etching" process known in the prior art and described in particular in U.S. Pat. No. 4,956,219, DE19536033 or CH701975.

This technology consists in irradiating a polymer film by means of energetic heavy ions, resulting in the formation of linear latent traces characterized by a local degradation of this polymer; these traces are then revealed in the form of pores by means of a selective chemical attack.

The membrane is beamed with heavy ions. The heavy ions pass through the entire thickness of the polymer film. In passing through the polymer, the heavy ions destroy or cut the polymer chains and thus form a clean straight opening through the material. The final alignment of the pores is determined by the angle of the beam relative to the polymer film during the irradiation process. The beam may thus be perpendicular to the polymer film or at any other angle.

In the next step, the film is passed through a bath of a strong acid such as nitric acid and the openings become pores after contact with alkaline solutions such as sodium hydroxide or potassium hydroxide.

Contrary to the rest of the film, these openings made by the ions allow the alkaline solution to pass through, said alkaline solution filling them and allowing the etching of the pores by removing the material (polymer) around these openings.

The pore size is controlled by the concentration of the alkaline solution, the contact time and the temperature of the solution.

If polyester or polycarbonate is used, the membrane obtained is hydrophilic and can either be used as it is or else be treated using surface treatment processes (plasma, spraying or coating).

The preparation of membranes according to this "track etching" technology is more precisely described in patents U.S. Pat. No. 4,956,219 and CH701975.

This technology enables the production of porous polymer membranes characterized in particular by a flat surface and a narrow cut-off threshold.

The advantage of using membranes obtained by this technology is the great accuracy of the pore size, of the number of pores, and of the shape of the pores.

The pores are preferentially cylindrical, but this technology can also make it possible to obtain pores of other shape, such as of conical shape.

Preferentially, the pores are aligned, and have an angle of between 10° and 45°, relative to the vertical, but can also have angles >45° or <10°. These angles are obtained according to the angler of the beam of ions during the beaming of the membrane.

This technology is applicable to various materials, such as polycarbonate (PC), polyester (PET) or polyimide (PI). Polyamide, poly(vinylidene fluoride), polyacrylate or polyolefins can also be used.

This method makes it possible to easily obtain pores with a controlled size of between 0.02 μm and 15 μm, a pore density of between $10^3$ pores/cm$^2$ and $10^{10}$ pores/cm$^2$ and membranes with a thickness of between 5 μm and 80 μm.

It is to be noted that, without the treatment to form pores on the biocompatible polymer, such polymer would remain impervious to any substance, and would not allow diffusion of the substance of interest from the inner part of the biocompatible organ to the outer part. The pores only allow the diffusion of substances that are below the cutoff (i.e. that are smaller than the pore diameter).

It is thus clear that the layer of the non-woven biocompatible polymer and layer of the porous biocompatible polymer are different layers, made of different materials, and presenting different properties (in particular with regards to the passing and diffusion of substances through each layer).

Other Layers

Before adding the priming layer (layer that will allow the binding of the heparin to the surface of the membrane), it is possible to add various layers of polymers (such as any hydrophilic polymer) to the surface of the membrane, and in particular on the surface of the porous polymer. These layers of polymer can be added by using the Layer-by-Layer deposition method.

Membrane Lamination

For greater mechanical stability, the porous biocompatible polymer membrane is reinforced using a membrane made of non-woven.

The combination of a non-woven polymer and of the porous membrane of biocompatible polymer is preferentially carried out by lamination, using methods known in the art, such as thermal lamination, with or without the presence of adhesives, preferably without adhesive.

Thus, the reinforcement of the membrane can be improved via a multilayer system alternating layers of woven or non-woven polymers and of biocompatible porous polymers. However, any degradation of the diffusion properties should be avoided.

In particular, the mechanical stability can be increased by combining a thin functional membrane which has a high pore density with a thick protective membrane which has a low pore density.

There is no limitation to the number of layers of polymers that can be used to manufacture the membrane.

It is also possible to perform a surface treatment of one or more of the polymer layer (porous polymer and/or non-woven polymer) such as plasma or corona treatment.

As illustrated in FIG. 8, which shows a membrane where a layer of a non-woven polymer is situated between two layers of porous polymers, one can easily to see the different individual and distinct layers and that the non-woven and porous layers are not identical or confused one with the other.

Physical Characteristics of the Biocompatible Membrane

In the preferred embodiment, the membrane according to the invention comprises two layers of porous biocompatible polymer, each covered with at least one hydrophilic polymer, which surround the layer of non-woven.

Pore Diameter and Density

As seen above, the pores are introduced into each of the layers of porous biocompatible polymer using methods known in the art. It is preferred for at least the layer (if it is the only one) or one of the two layers of porous biocompatible polymers to have a pore density greater than $10^6$ pores/cm$^2$, preferably greater than $10^7$ pores/cm$^2$. This pore density is generally less than $10^{11}$ pores/cm$^2$, preferably less than $10^{10}$ pores/cm$^2$. Use is therefore made of membranes which can have a pore density preferentially greater than $10^6$ pores/cm$^2$, more preferably greater than $10^7$ pores/cm$^2$. This density is preferentially less than $10^{11}$ pores/cm$^2$, or even less than $10^{10}$ pores/cm$^2$. This density is therefore between $10^6$ pores/cm$^2$ and $10^{11}$ pores/cm$^2$. A density greater than $10^9$ and less than $10^{10}$ pores/cm$^2$ is perfectly suitable.

As seen above, the pores of the layers of porous biocompatible polymer have an internal diameter such that they allow semi-permeability of the membrane.

Thus, at least one of the two layers (or the only layer if such is the case) of porous biocompatible polymer has pores which have an internal diameter greater than 5 and preferably greater than 10 nm, and less than 100 nm, and preferably greater than 10 nm and less than 50 nm, more preferably less than 40 nm. It has also been observed that a pore diameter of less than 90 nm at the surface of the membrane is also very favorable for this layer of porous biocompatible polymer, as such pore diameter maintains the semi-permeability property, that is sought for the membrane. The pore density is then advantageously greater than $2.10^9$ and less than $4.10^{10}$ pores/cm$^2$.

When the membrane has two layers of porous biocompatible polymers, the internal diameter of the pores of one of the layers is preferentially as above.

The internal diameter of the pores of the second layer may be larger, the cut-off effect at the desired size being given by the diameter of the pores of the first layer. Thus, the internal diameter of the pores of the second layer may be greater than 100 and less than 2000 nm, preferably greater than 200 nm. These pores preferably have an internal diameter less than 1000 nm. An internal pore diameter greater than 400 and less than 600 nm, or of approximately 500 nm, is perfectly suitable. The pore density is then advantageously greater than $5.10^6$ and less than $5.10^7$ pores/cm$^2$.

When the membrane comprises two layers of porous biocompatible polymer, which surround the layer of non-woven, it is preferable for the encapsulating chamber to be such that the layer for which the pore diameter is the smallest is situated inside the chamber (in contact with the secreting cells producing at least one substance of therapeutic interest) and that the layer for which the pore diameter is the widest is situated on the outside (in contact with the patient's body). In this embodiment, the heparin is at least present on the layer that is situated on the outside, although the layer situated in the inside may also be functionalized with heparin.

Membrane Thickness

In one preferred embodiment, the total thickness of the membrane (comprising the layer of non-woven polymer and the layer(s) of porous polymer(s)) is greater than 45 µm. It is generally, and preferably, less than 200 µm, but can also be greater than this size; thicknesses ranging up to 300 µm, or even beyond, can in particular be envisaged. Preferably, it is greater than 50 µm. It is also preferentially less than 150 µm. This membrane thus generally has a thickness of between 45 and 200 µm.

When the membrane has two layers of porous biocompatible polymers, said layers can have the same thickness or have different thicknesses.

The layer of non-woven polymer generally has a thickness greater than 40 µm, preferably greater than 60 µm, more preferably greater than 80 µm. This layer has a thickness generally less than 250 µm and preferably less than 150 µm. Thus, the thickness of the layer of non-woven polymer is often between 40 µm and 150 µm.

When the membrane has only one layer of biocompatible polymer, said layer then has a thickness greater than 5 µm. This layer is less than 200 µm, preferably less than 100 µm, being, however, preferably less than 50 µm.

When the membrane has two layers of porous biocompatible polymer, and said layers have different thicknesses, the thickness of the first layer is then greater than 5 µm. It is also preferably less than 200 µm, but preferably less than 40 µm; a thickness less than 15 µm (and preferably greater than 5 µm) is perfectly suitable. This thickness is preferentially the thickness of the layer which has pores with the smallest internal diameter, if the internal pore diameter is different for the two layers.

The thickness of the second layer is generally greater than 25 µm. It is preferably less than 200 µm, preferably less than 100 µm, more preferably less than 50 µm; a thickness of between 30 and 50 µm is perfectly suitable.

The thickness of each layer of hydrophilic polymer optionally present on one or the two layer(s) of porous biocompatible polymers is negligible, compared with the total thickness of the membrane. It is in fact preferably less than 500 nm and generally between 25 and 250 nm.

In one preferred embodiment, the membrane has two layers of porous biocompatible polymers on either side of a layer of non-woven polymer.

In this embodiment, one layer of porous biocompatible polymer has pores with an internal diameter greater than 100 nm, preferably greater than 200 nm, more preferably greater than 400 and less than 1000 nm, more preferably less than 600 nm, preferably at a density of about $5.10^7$ pores/cm². It is then advantageous for this layer to be the one with a thickness of between 25 and 200 µm (see above).

The other layer of porous biocompatible polymer has pores with an internal diameter greater than 5 nm, preferably greater than 10 nm (and generally less than 100 nm, preferably less than 50 nm, preferably less than 40 nm), preferably at a density of about greater than $2.10^9$ pores/cm². This density is also preferentially less than $7.10^9$ pores/cm².

It is advantageous for this to be the layer with a thickness of between 5 and 200 µm (preferably 5 to 15 µm).

Encapsulation Chamber

The invention also relates to a chamber for encapsulating secreting cells producing at least one substance of therapeutic interest, comprising a closed shell made of a functionalized membrane as above, delimiting a space capable of containing the secreting cells producing at least one substance of therapeutic interest. This encapsulating chamber can also be referred to as a "pouch" and makes it possible to form a bioartificial organ which is implantable in the patient. In this embodiment, the heparin-functionalized surface of the membrane is directed to the exterior (outer part) of the chamber.

In one particular embodiment, this encapsulating chamber also comprises a biocompatible sheet contained in said shell, said sheet preferably comprising projections (also designated as protuberances) at its surface. These projections are advantageous for maintaining a space for the cells between the sheet and the shell, but also for distributing the cells in a homogeneous and planar manner, thus making it possible to maximize the exchange surface. This sheet is preferentially made of silicone, and can be treated by any treatment known in the art to increase hydrophilicity thereof.

Such an embodiment is described in application WO 2012/010767. Thus, in one preferred embodiment, the shell is formed from two membranes as disclosed herein, which are heat-welded together. Use may be made of the method described in WO 2012/010767 or a method of heat-welding using ultrasound, known in the art. The method for forming the shell is simple and makes it possible to enclose the sheet in the shell.

Shape of the Chamber

In one preferred embodiment, the encapsulating chamber is circular. Such a shape has several advantages:
- absence of "corners" or protruding parts which are capable of creating cell or inflammatory aggregates during the implantation,
- ease of manufacture of the encapsulating chamber (no need to orient the two membranes and the sheet before the heat-welding).

In one particular embodiment, the diameter of the encapsulating chamber is greater than 3 cm, preferably greater than 5 cm, or than 8 cm. It is generally less than 20 cm, and is preferentially less than 15 cm, or than 14 cm. A diameter of between 8 and 14 cm is perfectly acceptable.

When the chamber is not round, the largest dimension thereof is generally greater than 3 cm, preferably greater than 5 cm, or than 8 cm. It is generally less than 20 cm, and is preferentially less than 15 cm, or than 14 cm.

Volume of the Chamber

As seen above, the encapsulating chamber preferentially makes it possible to manufacture a "macro" organ when the secreting cells producing at least one substance of therapeutic interest are introduced therein, i.e. it allows said cells to secrete this substance for a considerable period of time (greater than 3 months, preferentially greater than 6 months) at levels which are of physiological interest (i.e. making it possible to meet the patient's need). The encapsulating chamber should therefore be able to receive a large number of cells.

It is generally estimated that the preferred internal volume of the encapsulating chamber should be greater than 15 ml, preferably greater than 20 ml, more preferably greater than 25 ml, and can rise to 50 ml, for use in humans. For use in other animals, the volume will be different (approximately 0.5 to 1 ml in rats, for example).

Such encapsulating chambers must be able to contain a large number of cells. In the context of the treatment of diabetes, it must be possible to encapsulate the equivalent of at least 300 000 islets of Langerhans, preferably the equivalent of more than 500 000 islets, and optionally up to the equivalent of one million islets of Langerhans. In the knowledge that one islet contains, on average, about 1000 cells, this gives an estimation of the number of cells that the encapsulating chamber according to the invention can contain.

The number of cells will obviously vary according to the type of cells that it is desired to encapsulate and implant in the patient.

In one preferred embodiment, the membrane forming the encapsulating chamber comprises two layers of porous biocompatible polymers on either side of the non-woven polymer. In this embodiment, it is preferred for at least the internal layer (situated inside the chamber after formation of the chamber) to be the layer on which the pores provide the semi-permeable nature of the membrane (cut-off threshold), i.e. which has the pores that have an internal diameter greater than 5 nm (and generally less than 100 nm) or having the other dimensions mentioned above. In this embodiment, it is preferred when each layer of porous biocompatible polymer is heparinized. Alternatively, only the layer of porous biocompatible polymer that is in contact with the outer part of the chamber is heparinized.

The layer external to the shell (in contact with the patient's tissues and cells) can have pores with a larger internal diameter, in particular greater than 100 nm, but preferably less than 2000 nm, or having the other dimensions mentioned above. This external layer is functionalized with heparin as disclosed above.

In one embodiment, and as described in WO 2012/010767, the encapsulating chamber can comprise at least one connector (in particular attached to the shell and/or the sheet), which makes it possible to establish a communication between the exterior and the interior of the shell. Connecting these connectors to flexible tubes makes it possible to fill and empty the chamber, in particular if the cells are dead.

One should note that it is possible to functionalize (heparinize) the membranes before forming the encapsulation chamber. In this case, as indicated elsewhere, the heparin should be, at least, on the outer surface of the chamber.

Alternatively, it is possible to form the chamber and then functionalize (heparinize) it, for instance by dipping it in various baths containing the priming solution, and the heparin solution.

Bioartificial Organ

A bioartificial organ comprising at least one encapsulating chamber according to the invention is also part of the invention. Such a bioartificial organ also advantageously presents the tubes connected to the connectors and making it possible to fill and empty the bioartificial organ, making it possible to renew the content of the bioartificial organ when it is implanted in a patient, without performing an explantation.

This bioartificial organ may contain various cell types.

Cells Encapsulated in the Bioartificial Organ

The cells present in the bioartificial organ produce at least one biologically active substance of interest. They can in particular be insulin-secreting cells or islets of Langerhans, which produce insulin, when the encapsulating chamber is intended for the manufacture of a bioartificial pancreas.

The cells may also be hepatic cells when the encapsulating chamber is intended for the manufacture of a bioartificial liver.

In one particular embodiment, the cells are transfected or transformed with at least one nucleic acid allowing the expression of a biologically active substance of interest. Among the biologically active substances of interest, mention may be made, by way of illustration, of insulin, cytokines, peptide hormones, growth hormone, coagulation factors VIII and IX and calcitonin.

Generally, the term "biologically active substance" is intended to mean a substance which is released or secreted by the cell which produces it and which exerts its effect on a target cell or a target molecule in the host organism, for instance a neurotransmitter, a hormone, a growth factor, a coagulation factor or a cytokine.

A great diversity of cells can be used, including immortalized cell lines, for instance primary cultures of dividing cells, or else pluripotent stem cells.

The cells can, for example, be myoblasts, which are cells that are precursors of muscle cells derived from the stem cell populations of the mesoderm, and which can be easily transformed with a nucleic acid allowing the expression of the biologically active substance of interest. Those skilled in the art may advantageously refer, for example, to WO 94/02129, WO 93/03768 or WO 90/15863.

Preferably, the cells contained in an encapsulating chamber are embedded in a matrix, such as a matrix of collagen type IV or of fibrin, where appropriate in combination with laminin, entactin and heparan sulphate.

The cells contained in an encapsulating chamber can generally be embedded in a matrix composed of any product or combination of products allowing the immobilization of these cells in a viable form.

The cells producing at least one biologically active substance of interest can also be encapsulated in an alginate matrix.

Manufacture of an Encapsulating Chamber

The encapsulating chamber is manufactured by any method known in the art.

Use is preferably made of the teaching of WO 2012/010767, which should be considered to be an integral part of the present application.

The invention thus relates to a method for manufacturing an encapsulating chamber according to the invention, comprising a step of heat-welding two membranes according to the invention (or even a folded membrane), in such a way as to form a pouch intended to receive cells producing at least one biologically active substance of interest.

In one particular embodiment, as seen above, the encapsulating chamber contains a sheet, and also one or more connectors. The method for manufacturing such a pouch is described in WO 2012/010767. The reader is invited to refer to WO 2012/010767 for more detailed explanations regarding the process for manufacturing the encapsulating chamber.

The invention also comprises a process for obtaining a heparin-functionalized biocompatible semi-permeable membrane, comprising the steps of:
  a. providing a semi-permeable membrane comprising at least one layer of porous biocompatible polymer, and one layer of non-woven biocompatible polymer
  b. applying a treatment to said layer of porous biocompatible polymer in order to make it cationic
  c. contacting a conjugate consisting of a substantially straight-chained organic polymer having a number of functional groups distributed along the polymer backbone chain, via which groups at least 20 molecules of heparins are anchored through covalent bonds, wherein the heparins are bound to the polymer backbone chain via an amino group or amino acid associated with the heparins, such that said conjugate is bound substantially irreversibly to said treated layer of porous biocompatible polymer, in that the conjugate has a polyanionic character and that the treated layer of porous biocompatible polymer is cationic.

The invention also relates to a process for obtaining a heparin-functionalized biocompatible semi-permeable membrane, comprising the steps of:
a. providing a semi-permeable membrane comprising at least one layer of porous biocompatible polymer, and one layer of non-woven biocompatible polymer
b. applying a treatment to said layer of porous biocompatible polymer in order to provide primary amino groups on the surface of said layer of porous biocompatible polymer
c. reacting said treated surface presenting primary amino groups with heparin, modified to contain complementary functional groups, so as to form covalent bonds between said primary amino groups and said complementary functional groups.

In either method, steps b) and c) can be applied by dipping the membrane in appropriate solutions. In this case, both faces of the membranes shall be functionalized with heparin.

Alternatively, one can mask a face of the membrane before dipping in step b), or perform step b) by flowing an appropriate solution only on the fact that needs to be heparinized. In this embodiment, only one face of the membrane would be heparinized.

EXAMPLES

Figure 1:
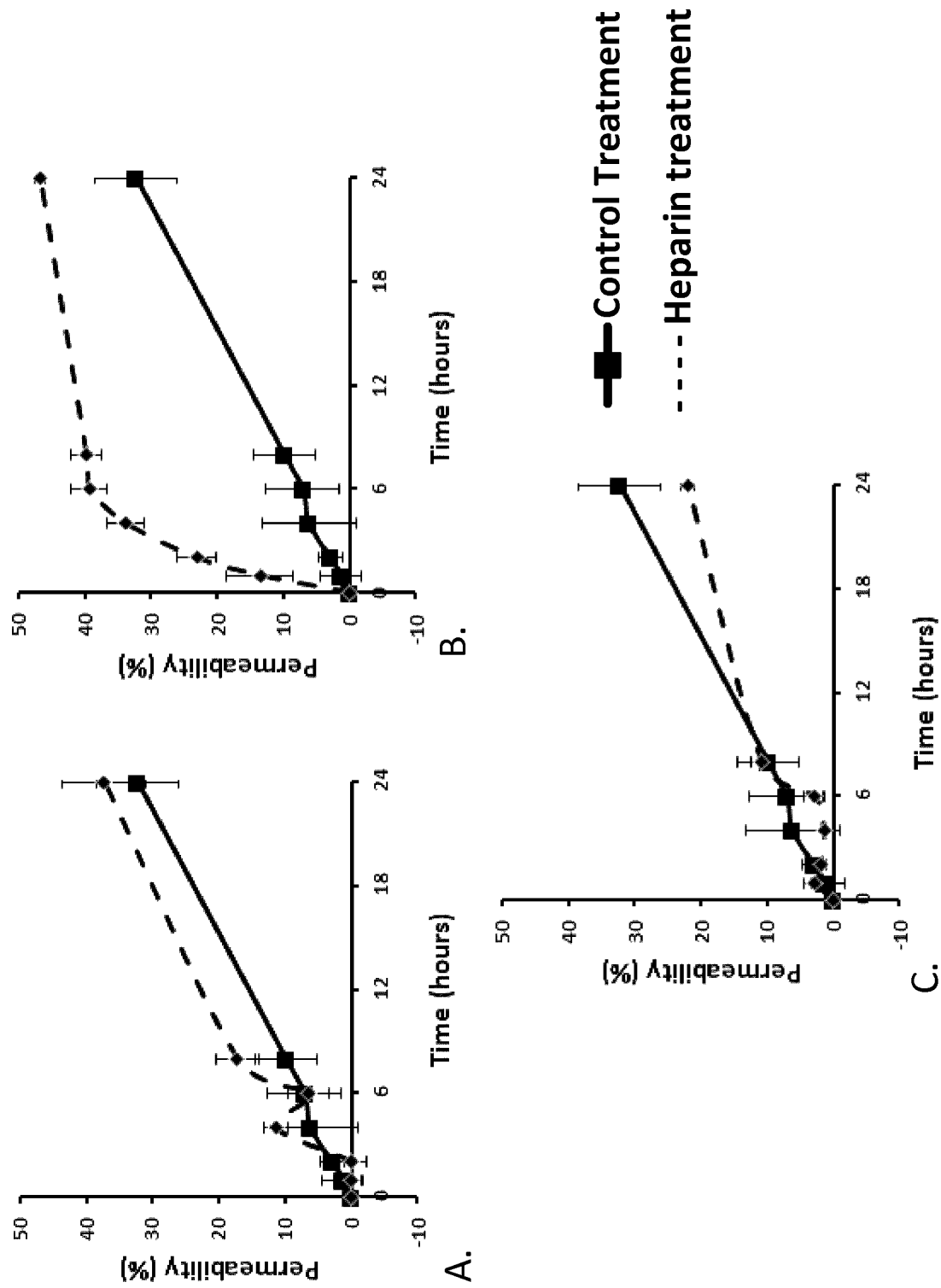
FIG. 1: static diffusion kinetics of insulin through membranes treated using three different (increasing) concentrations Conc 1 (A); Conc 2 (B) and Conc 3 (C) compared to control treatment including heparin within a hydrophilic polymer (according to EP 2575914) (n=3 for each condition).

Example 1: Preparation of Conjugates of Heparin (According to Example 1 of EP 658 112)

Heparin is dissolved in phosphate buffer, pH 7.5, (200 mg/4 ml), to which 1 ml of SPDP (10 mg/ml MeOH) is added under stirring, and the reaction is allowed to proceed for 20 minutes.

The SPDP-substituted heparin thus obtained is purified on Sephadex® G-25 (Pharmacia LKB Biotechnology AB, Sweden). To 100 μl of the obtained sample are added 900 μl of dithiothreitol (DTT, 10 mg/ml), and the obtained absorbance is measured spectrophotometrically at 343 nm.

SPDP coupled to heparin is reduced to SH by the addition of DTT and subsequent chromatographical purification.

Polylysine having a molecular weight of 450,000 is dissolved in water (20 mg/3 ml), to which 2 ml of SPDP (10 mg/ml MeOH) are added, and the reaction is allowed to proceed under shaking for 20 minutes. Purification is performed on Sephadex® G-25 (Pharmacia LKB Biotechnology AB, Sweden) with 0.15 M NaCl as eluent. The void fraction is tested with DTT, the substitution-degree being determined as 158 SPDP-groups per molecule of polylysine.

The above prepared solutions of heparin-SH and polylysine-SPDP, respectively, are adjusted to 3 M NaCl and mixed in such proportions that a ten percent excess of SH-groups in relation to SPDP-groups is obtained, and the reaction is allowed to proceed overnight. Completion of the reactions is determined by spectrophotometrical measurement of the release of thiopyridone at 343 nm. The preparation is purified on Sephacryl® S-500 (Pharmacia LKB Biotechnology AB, Sweden) with 0.5 M NaCl as eluent, the heparin-polylysine conjugates emerging as a void peak with baseline separation to free heparin.

The content of heparin is determined with the Orcinol assay described in Larsson, R., et al., Biomaterials 10 (1989) 511-516.

Example 2: Coating of the Membrane

The multi-layered membrane is primed by immersion in a solution of an agent for making it cationic (polymeric cationic amine such as polyethylenimine, polyallylamine, chitosan or polylysine in borate buffer (pH 9)) then rinsed four times with MilliQ water.

The conjugate as prepared in Example 1 is then applied by immersion of the membrane in a solution containing said conjugate (0.05 mg/ml). The membrane is then rinsed with water and rinsing buffer such as borate buffer, pH 9, and water.

The priming/coating/rinsing steps may be performed more than once (once, twice or even three times), in order to obtain a concentration of 0.2-0.8 μg/cm$^2$ (corresponding to 0.1-0.4 UI/cm$^2$).

Different conjugates containing different amounts of heparin, thus leading to concentrations of heparin (Conc 1, Conc 2 and Conc 3) are used.

The membranes are then dried and used for future experiments.

The membranes thus obtained are heparinized with heparin covalently bound to an organic polymer, to form a conjugate which is then irreversibly attached to the membrane surface (made cationic) by means of multiple ionic interactions.

Example 3: Preparation of Heparin for End-Point Attachment (According to Example 2 of EP 86186)

A solution of heparin in 300 ml water is cooled to 0° C. on an ice bath. Sodium nitrite 10 mg is added with stirring. Then acetic acid is added drop-wise (2 ml). The solution is allowed to stand under stirring for two more hours at 0° C.

The reaction mixture is worked up by dialysis against distilled water and lyophilization.

Example 4: Coating of Membrane with Heparin as Prepared in Example 3

Surface of the membrane is covered by a layer of a substrate containing primary amino groups (such as a polyamine, in particular a polymeric aliphatic amine, especially polyethylene imine).

After renewed rinsing the membrane is incubated with a solution of heparin diazotized as in Example 2 (20 mg/ml) (a) or 2 mg/ml (b) and sodium cyanoborohydride (0.5 mg/ml) in a phosphate buffer pH 7.0 for 24 hours at room temperature. The heparinized membrane is finally carefully rinsed with water.

The membrane is then dried and used for future experiments.

The membrane thus obtained is heparinized with heparin covalently bound to the polyamine layer at the surface of the membrane.

Example 5: Membrane Permeability to Glucose, Insulin and Immunoglobulin (IgG) (Membranes Coated According to Example 2)

Permeability of coated membranes to glucose, insulin and IgG were performed as follows, using diffusion chamber including a lower part and an upper part separated by membrane to test:

Solutions

The three molecules of interest tested are diluted in Phosphate Buffer Solution (PBS)

Glucose (4 g/L)

Dissolve 240 mg of glucose (Fischer, ref: G/0500/53) in 60 mL of PBS

FITC-IgG (13 µg/mL)

Add 34.5 µL of FITC-IgG stock solution at 10 mg/mL (Sigma, ref: F9636) to 59,966 mL of PBS.

Insuline (10 µg/mL)

Add 600 µL of FITC-Insulin stock solution at 1 mg/mL (Sigma, ref: I3661) to 59,400 mL of PBS.

Protocole

Lower compartment of diffusion chamber is filled using 3 mL of PBS and membrane to test is placed onto the lower compartment, in contact with the liquid without air bubble. Upper compartment is then firmly screwed on the lower part and filled with 3 mL of solution containing molecule of interest. Chamber is then closed using a cap, and incubated at 37° C. for 1 to 24 hours. After incubation, 1 mL of solution is taken in the upper part then in lower part after retrieving of the membrane.

Concentration of FITC-Insulin and FITC-IgG are determined against calibration curve using fluorescence intensity measurement (Excitation wavelength: 475 nm, Emission wavelength: 500 to 550 nm). Glucose concentration is assessed by enzymatic method using Glucose RTU® kit (BioMérieux, ref: 61 269). Results are expressed as follows:

$$\text{Permeability}(\%) = (C_{Lower\ compartment} / C_{Upper\ compartment} + C_{Lower\ compartment}) \times 100$$

C: Glucose, IgG or Insulin concentration.

At the equilibrium, concentration is the same in both compartments, corresponding to a permeability of 50%.

FIG. 1 shows that a clear difference on kinetics is observed only with heparin at Conc 2 which improves diffusion of insulin compared to control treatment.

Figure 2:
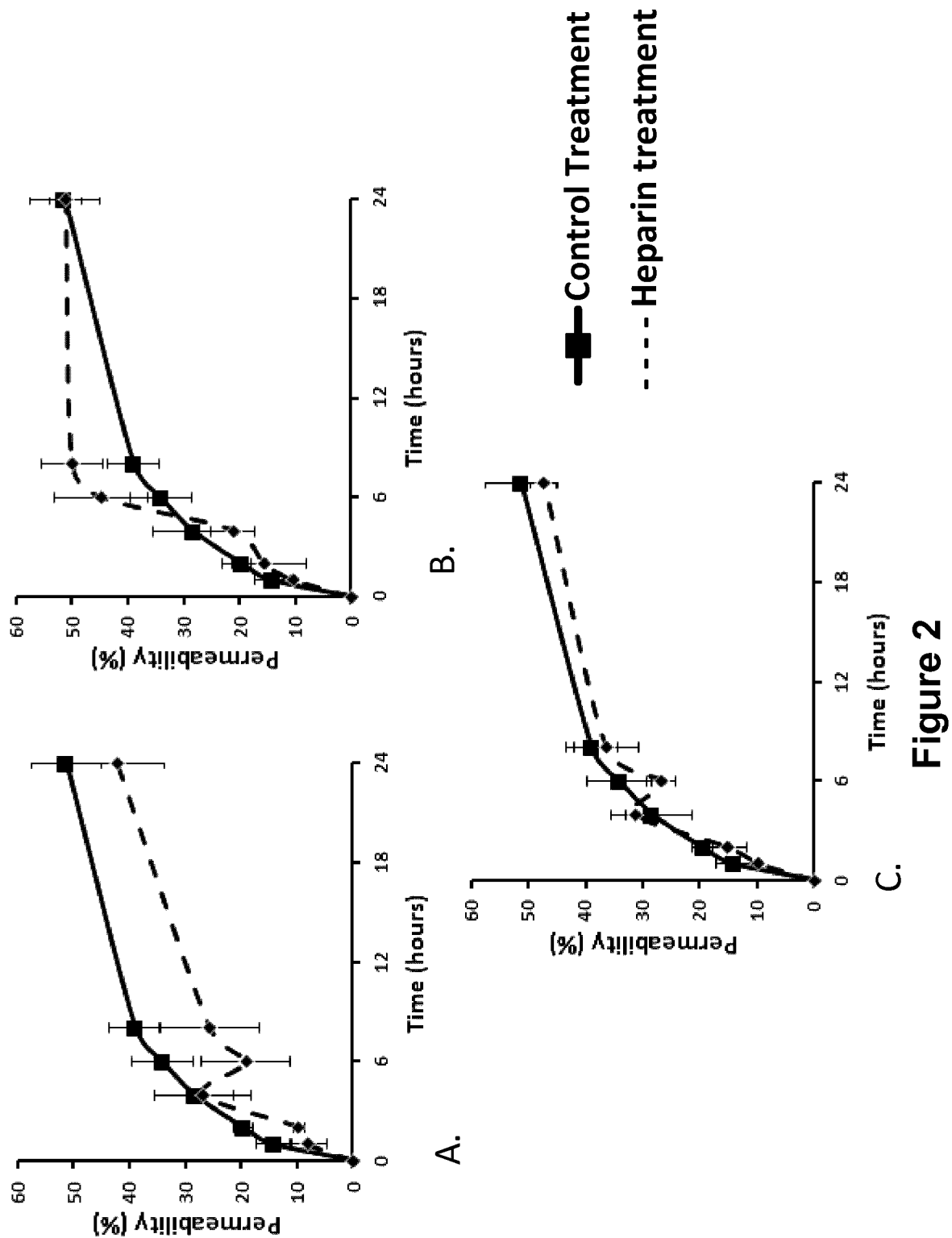
FIG. 2: static diffusion kinetics of glucose through membranes treated using increasing concentrations of Heparin: Conc 1 (A); Conc 2 (B) and Conc 3 (C) respectively compared to control treatment including heparin associated with hydrophilic components (according to EP 2575914) (n=3 for each condition).

FIG. 2 shows that Kinetics are comparable even if diffusion tends to be faster with heparin at Conc 2 compared to other conditions.

Figure 3:
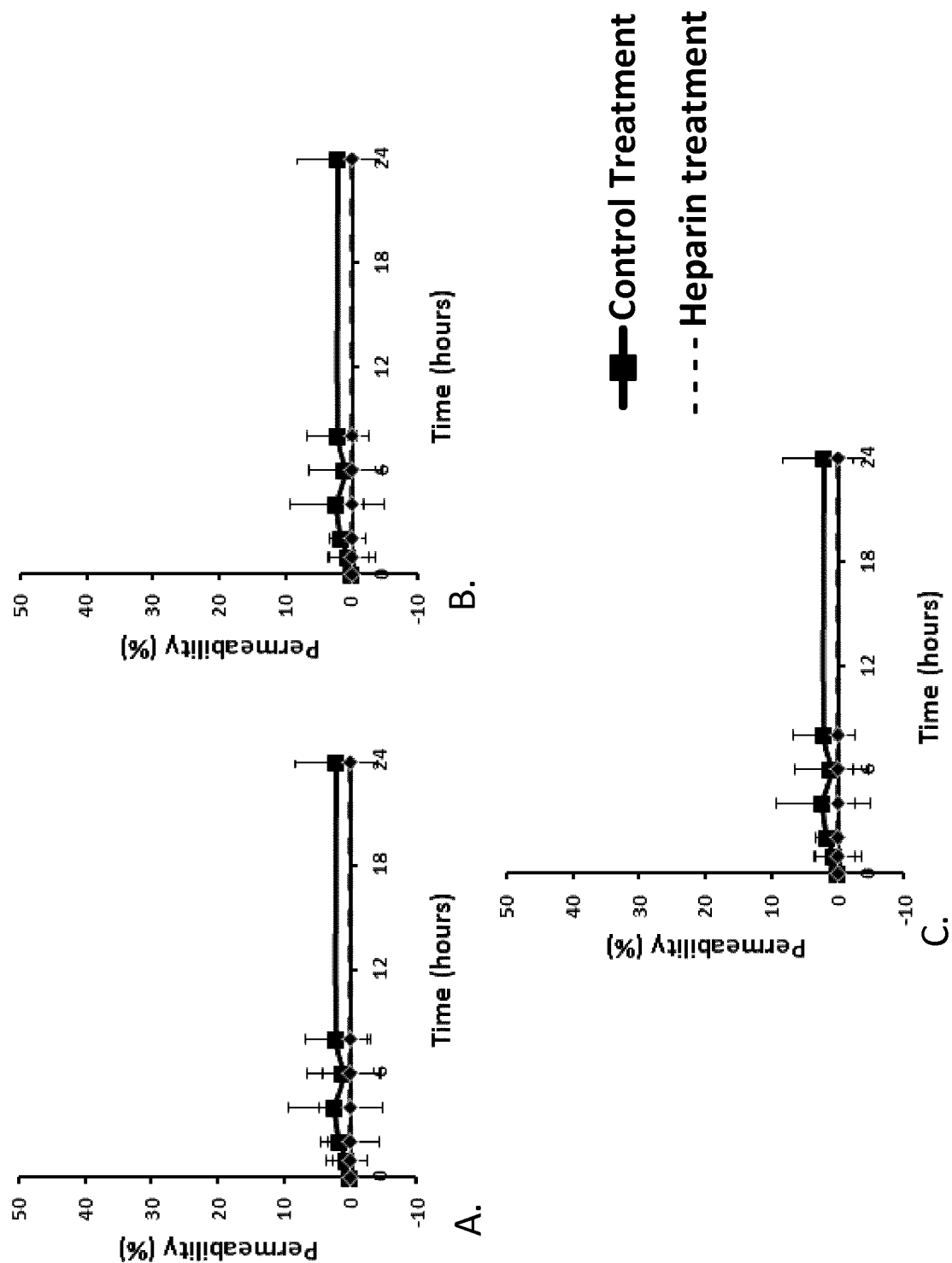
FIG. 3: static diffusion kinetics of IgG through membranes treated using Conc 1 (A); Conc 2 (B) and Conc 3 (C) compared to control treatment (EP 2575914) (n=3 for each condition).

FIG. 3 shows a perfect rejection of IgG without differences between treatment tested.

Example 6: Biocompatibility of Coated Membrane (According to Example 2) in Rat Membrane Implantation and Retrieving Wistar rats (weight: 200-250 g) are anesthetized using isoflurane and placed in dorsal decubitus. A 2 $cm^2$ area is shaved in the lower part of abdomen and disinfected using povidone iodine. In the disinfected area, an incision of 0.8 cm is performed in skin and abdominal muscles, and a piece of membrane (1 $cm^2$) is placed into the epididymal fat pad. Wound is closed using 4-0 suture string and rat is allowed to wake up and recover, with appropriate antibiotic and antalgic treatment.

After a given time, rats are sacrificed using lethal dose of pentobarbital and membrane is retrieved together with surrounding tissues which are placed in buffered formol.

Histological Analysis

Fixated tissues are washed two times in PBS and dehydrated using increasing concentrations of ethanol (70% 2×10 min; 95% 3×15 min; 100% 2×30 min). Tissues are then impregnated in toluene (3×15 min) and paraffin (3×20 min) and embedded in fresh paraffin.

Tissues are then cut using microtome with a thickness of 4 µm and stained with Hematoxylin-Eosin and Masson's Trichrome. Representative pictures are taken and different parameters are quantified.

Fibrosis thickness in the tissue surrounding the membrane: three measurements on three non-overlapping fields (magnification: ×10)

Vessel surface and number: measurement and count on six non-overlapping fields (magnification ×10).

The results of histological analysis on tissues surrounding membranes pieces implanted in epididymal fat pad of rats for 14 days are as follows:

Membranes were previously coated with control treatment including heparin within a hydrophilic polymer (as described in EP 2575914), Conc 2 or Conc 3. Hematoxylin-eosin staining highlights a lower cell infiltration in the area in contact with membrane coated with Conc 2. Masson's trichrome staining shows that heparin at Conc 2 increases vessel size and tends to reduce the thickness of fibrotic tissue around the membranes.

Figure 4:
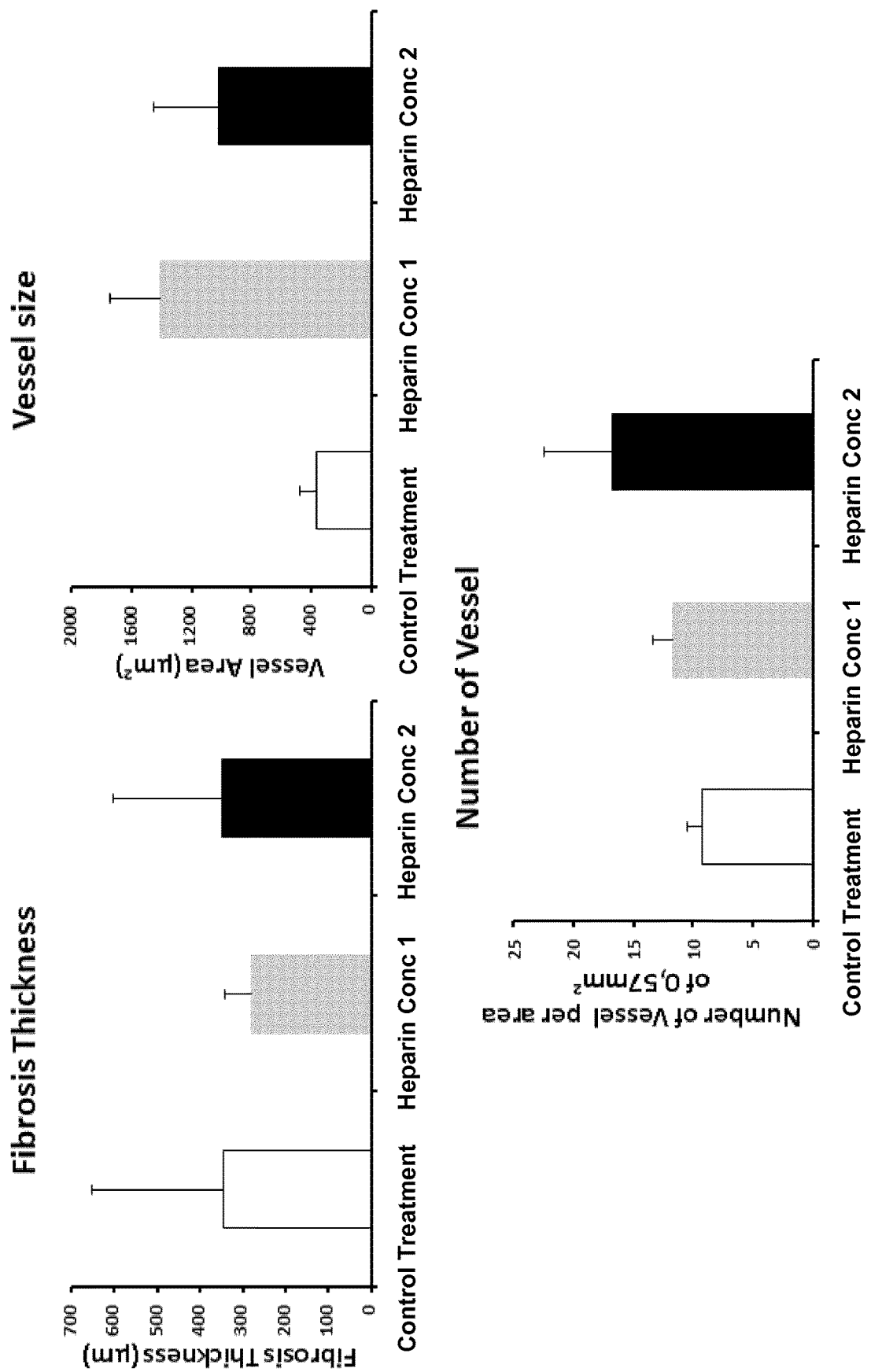
FIG. 4: quantifications on tissues surrounding membranes' pieces implanted in epididymal fat pad of rats for 14 days and stained with Masson's trichrome.

FIG. 4 shows that treatment with heparin (Conc 2) has no clear effect on fibrosis but significantly increase vessel size compared to control treatment (Patent EP2575914) ($p=0.0116$; student t test). Number of vessels tends also to increase with the two heparin treatments, compared to control.

Example 7: Surface Analyses on Membrane (Coated According to Example 2)

ToF-SIMS Analysis

ToF-SIMS analyses were performed on coated membranes and signal obtained were normalized using values obtained on crude membrane. Characteristic secondary ion patterns enable to detect membrane polymer, cellulosic polymer and heparin.

Contact Angle

Contact angle is measured on membranes with ultrapure water, using the sessile drop method, in static conditions. Briefly, a 10 µL drop is deposited on the surface of the membrane using a needle. Drop shape is then analyzed, to determine angle between the surface and the outline of the contact surface.

Figure 5:
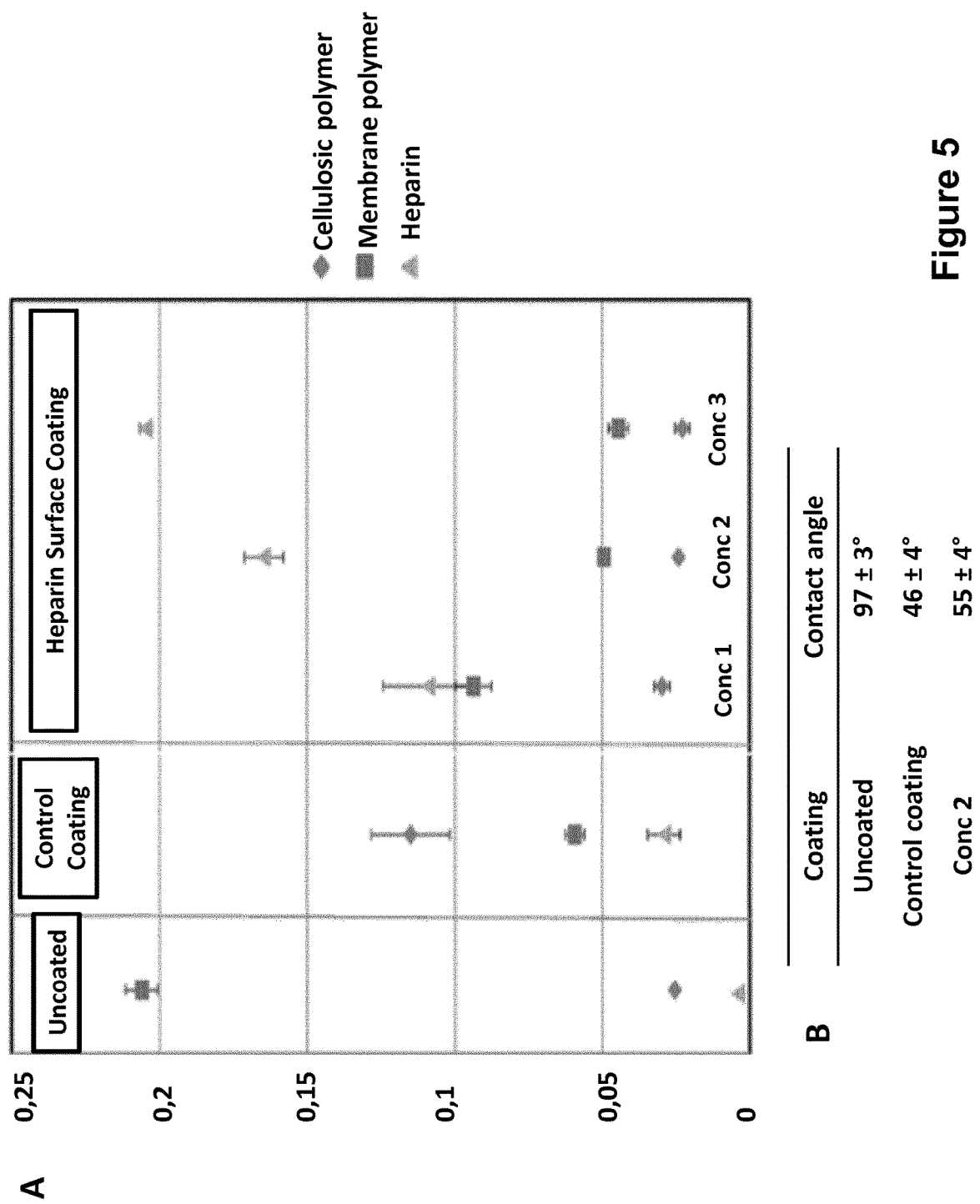
FIG. 5: presents results of surface analyses on coated membranes. A. shows ToF-SIMS. B. shows contact angle of membranes.

FIG. 5 presents results of surface analyses on coated membranes. Chart A shows ToF-SIMS analyses indicating that both type of coatings induce a dramatical decrease in signal intensity of membrane polymer, compared to uncoated membrane. Heparin is detected with coating according to example 2, but not in control coating (EP 2575914) where signal seems to be masked by cellulosic excipient. Chart B shows contact angle of membranes, indicating a similar decrease with the two coatings, compared to uncoated membrane.

Anti-Thrombin Binding Test

1 $cm^2$ pieces of membrane are incubated with purified anti-thrombin (AT) solution. After extensive rinsing, bound AT was removed from the membrane using Heparin at 150 UI/mL in physiological water. The anti-thrombin activity of the obtained solution is assessed with a factor Xa inhibition assay. Purified Xa factor is added to the sample and resulting solution is incubated 90 seconds at 37° C. A chromogenic substrate of factor Xa is thus added (substrate S-2765 Chromogenics, Mölndal, Sweden), and reaction is stopped after 90 seconds of incubation at 37° C. with 2% citric acid solution. Finally, remaining factor Xa activity is quantified by absorbance measurement at 405 nm and linked to anti-thrombin binding capacity using a standard curve obtained with known concentration of anti-thrombin.

Figure 6:
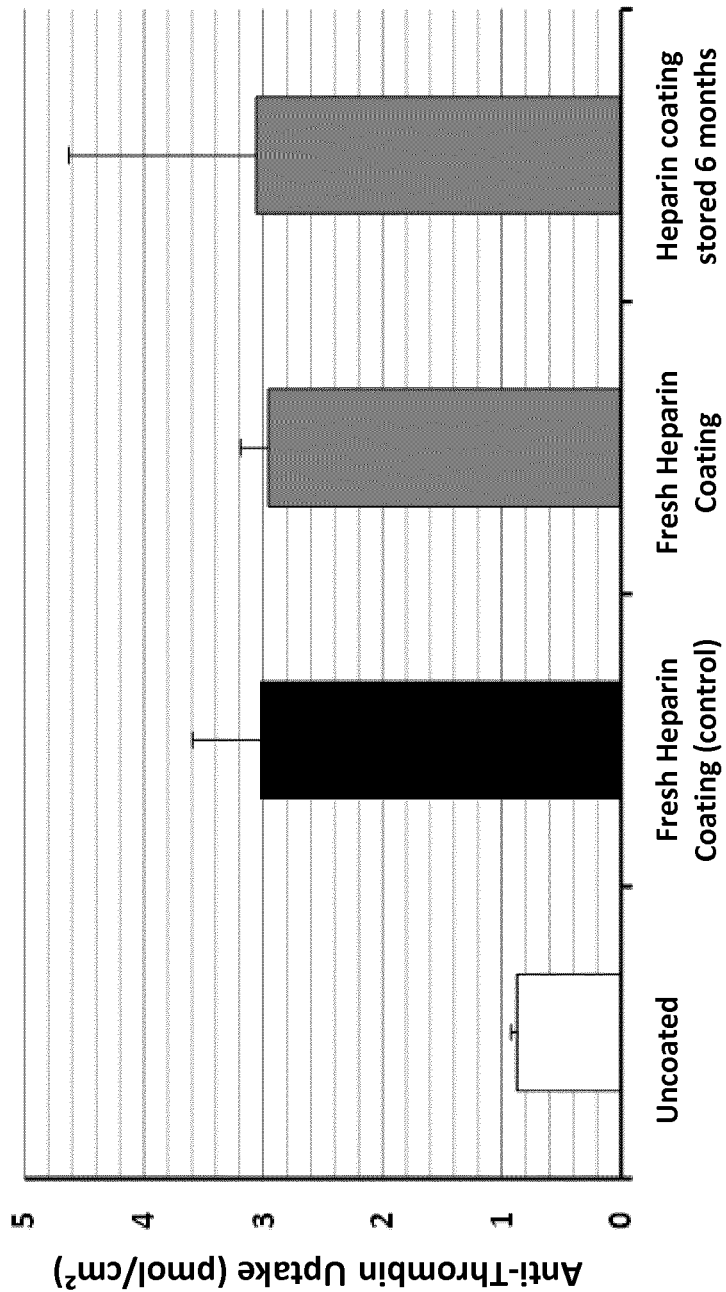
FIG. 6: Anti-thrombin (AT) uptake test results for uncoated (white), freshly coated with heparin according to EP 2575914 (black) freshly coated with heparin (Conc 2) and 6 months storage after coating (grey).

FIG. 6 shows Anti-thrombin (AT) uptake test results for uncoated, freshly coated with Heparin (Conc 2) and 6 months storage after coating. An increase in AT uptake can be seen with fresh coating, which is not decreased after 6 months of storage. This highlights a good stability of the Heparin coating on the membranes.

Example 8: Activated Clotting Time (ACT) Assessment in Pigs

Göttingen minipigs were implanted with device featuring membranes coated with Heparin (Conc 2).

Briefly, a premedication is performed by intramuscular injection of Azaperone (Stresnil®—2 mg/Kg) and Ketamine (Imalgene®—10 mg/Kg). Anesthesia is induced with intravenous injection of 0.4 mg/Kg of Propofol ((2,6 di-isopropylphénol) and completed by a muscle relaxant Pancuronium at 0.1 mg/Kg. Immediately after induction, an orotracheal intubation is performed and a pulmonary ventilation is set up using a semi-closed circular system connected on a respirator in a controlled-pressure mode. The maintenance of anesthesia is ensured on the inhalatory mode using isoflurane (inspired fraction=2 vol %) with a fresh gaz debit of 2 L/min of a mixture of O2/N2O 50%/50% that serves as a vector gaz.

After shaving and disinfection of swine's abdomen, a midline incision is performed and a pouch is carefully dissected between the peritoneum and abdominal muscles. Device is then wetted with sterile saline solution and inserted into the pouch and attached at 4 points on abdominal muscles using 3/0 adsorbable thread. Abdominal muscles and subcutaneous tissue are then sutured by simple overlock using 1/0 and 3/0 adsorbable thread respectively. Finally, skin is closed by intradermal suture using 3/0 adsorbable thread.

At different time post-implantation blood samples are collected in citrated tubes. Platelet-poor plasma is prepared by two successive centrifugations at 2000 g during 10 min and stored at −80° C. until analysis. Once all samples collected, ACT were measured using a STA-R (Stago Group) analyzer.

Figure 7:
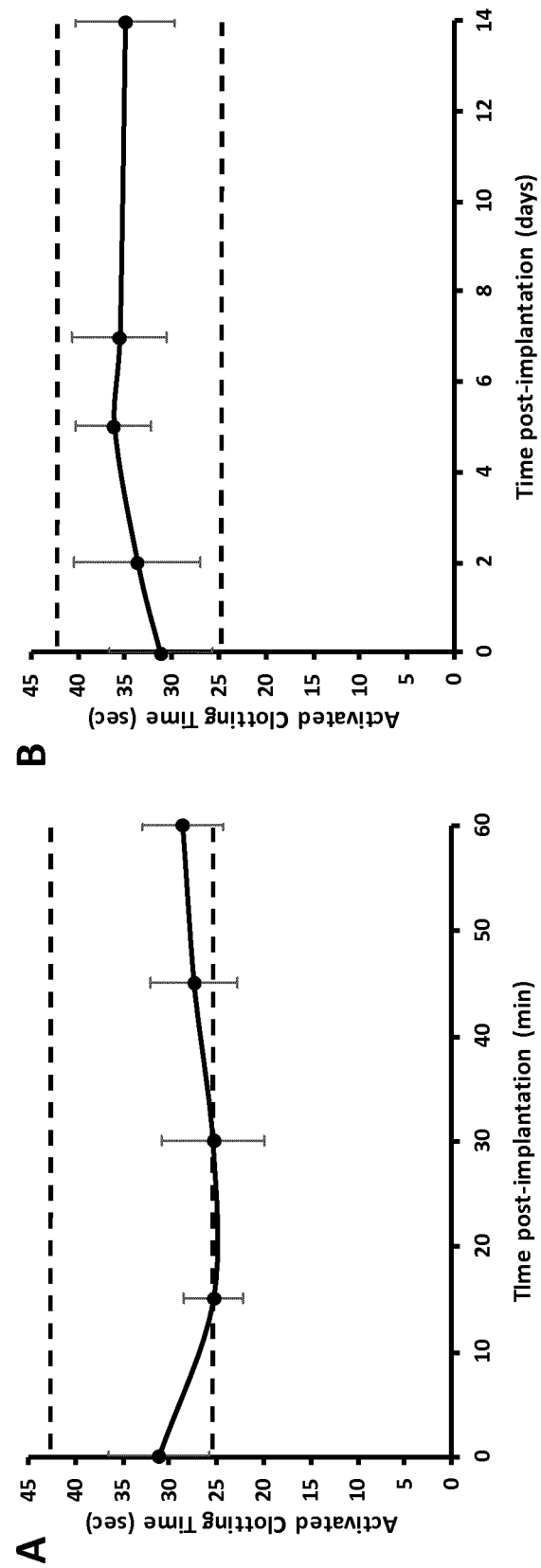
FIG. 7: Evolution of activated coagulation time after implantation of device coated with heparin (Conc 2).
Figure 8:
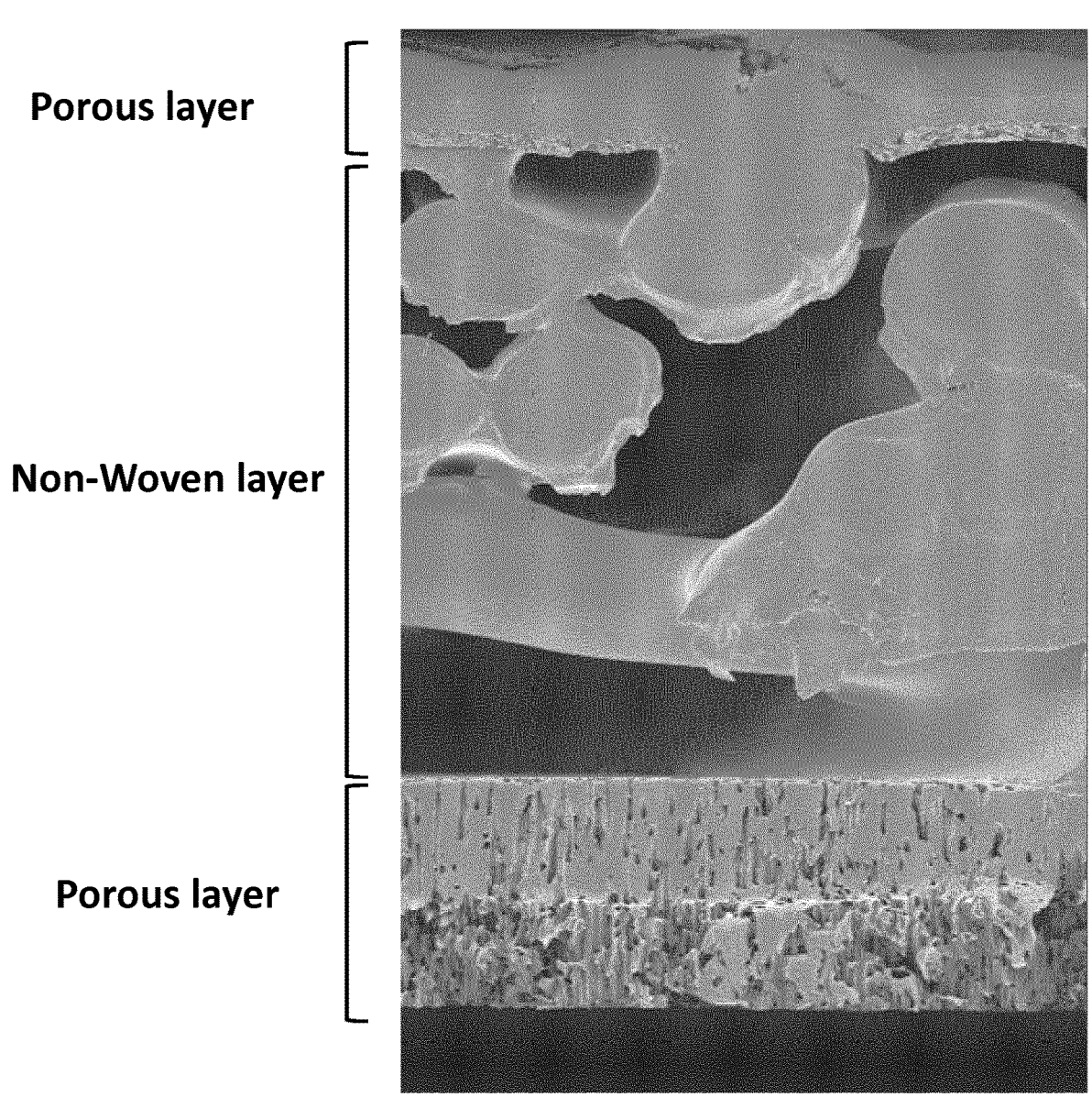
FIG. 8: Scanning Electron Microscope (SEM) pictures highlighting the different layers of a semi-permeable membrane. A first porous layer is visible at the top of the image and a second porous layer at the bottom of the image. A non-woven layer is located between the two porous layers.

As shown in FIG. 7, no significant raise is observed following device implantation, either just after implantation (FIG. 7.A) or a during the following days (FIG. 7.B), revealing an absence of systemic effect of the heparin from the coating. Results are expressed as mean±SD (n=6 animals) and horizontal lines show value range for a healthy (non-implanted) animal.

Example 9: SEM Analysis on Membrane Cross Section

Semi-permeable membranes were frozen-factured after rapid immersion in liquid nitrogen. Section were then attached on a support using carbon conductive cement and coated with Palladium-Gold, then carbon for subsequent observation in SEM. Observation were performed at 3.00 KV.

The invention claimed is:

1. A heparin-functionalized biocompatible semi-permeable membrane, wherein said membrane comprises a layer of biocompatible non-woven polymer located between two layers of porous biocompatible polymers and wherein heparin is bound, through covalent or ionic/electrostatic bonds on the surface of at least one porous biocompatible polymer to form a heparin layer.

2. The semi-permeable membrane according to claim 1, wherein said heparin layer is formed by a substantially straight-chained organic polymer having a number of functional groups distributed along the polymer backbone chain, via which groups at least 20 molecules of heparins are anchored through covalent bonds, wherein the heparins are bound to the polymer backbone chain via an amino group or amino acid associated with the heparins, and wherein said heparin layer is affinity bound to the surface of said layer of porous biocompatible polymer.

3. The semi-permeable membrane according to claim 1, wherein said heparin layer consists of heparin molecules covalently bound to a layer of a polymer applied on the surface of said layer of porous biocompatible polymer.

4. The semi-permeable membrane according to claim 1, wherein said non-woven polymer is chosen from polycarbonate (PC), polyester, polyethyleneimine, polypropylene (PP), poly(ethylene terephthalate) (PET), poly(vinyl chloride) (PVC), polyamide and polyethylene (PE).

5. The semi-permeable membrane according to claim 1, wherein in that said porous biocompatible polymer of at least one layer is chosen from polycarbonate (PC), polyester, polyethyleneimine, polypropylene (PP), poly(ethylene terephthalate) (PET), poly(vinyl chloride) (PVC), polyamide and polyethylene (PE).

6. The semi-permeable membrane according to claim 1, wherein one of the two layers of porous biocompatible polymers has a pore density of between $10^6$ pores/$cm^2$ and $10^{11}$ pores/$cm^2$.

7. The semi-permeable membrane according to claim 1, wherein the total thickness of the membrane is between 45 µm and 200 µm.

8. The semi-permeable membrane according to claim 1, wherein the thickness of one of the layers of biocompatible polymer is between 5 and 40 µm, and the thickness of the other layer of biocompatible polymer is between 25 and 100 µm.

9. The semi-permeable membrane according to claim 1, wherein the internal diameter of the pores present on one of the layers of biocompatible polymer is between 5 and 100 nm, and the internal diameter of the pores present on the other layer of biocompatible polymer is between 100 and 2000 nm.

10. A chamber for encapsulating secreting cells producing at least one substance of therapeutic interest, comprising a closed shell made of the semi-permeable membrane according to claim 1.

11. The chamber according to claim 10, wherein the layer external to the shell having pores with an internal diameter of between 100 and 2000 nm, and the layer internal to the shell having pores with an internal diameter of between 5 and 100 nm.

12. The chamber according to claim 10, which also comprises at least one connector which makes it possible to establish a communication between the exterior and the interior of the shell.

13. A process for obtaining the heparin-functionalized biocompatible semi-permeable membrane according to claim 2, comprising the steps of:
   a. providing a semi-permeable membrane comprising a layer of biocompatible non-woven polymer located between two layers of porous biocompatible polymers;
   b. applying a treatment to one layer of porous biocompatible polymer in order to make it cationic;
   c. contacting a conjugate consisting of a substantially straight-chained organic polymer having a number of functional groups distributed along the polymer backbone chain, via which groups at least 20 molecules of heparins are anchored through covalent bonds, wherein the heparins are bound to the polymer backbone chain via an amino group or amino acid associated with the heparins, such that said conjugate is bound by affinity to said treated layer of porous biocompatible polymer, in that the conjugate has a polyanionic character and that the treated layer of porous biocompatible polymer is cationic.

14. A process for obtaining the heparin-functionalized biocompatible semi-permeable membrane according to claim 3, comprising the steps of:
   a. providing a semi-permeable membrane comprising a layer of biocompatible non-woven polymer located between two layers of porous biocompatible polymers;
   b. applying a treatment to one layer of porous biocompatible polymer in order to provide primary amino groups on the surface of said layer of porous biocompatible polymer;
   c. reacting said treated surface presenting primary amino groups with heparin, modified to contain complementary functional groups, so as to form covalent bonds between said primary amino groups and said complementary functional groups.

15. The semi-permeable membrane according to claim 1, wherein the internal diameter of the pores present on one of the layers of biocompatible polymer is between 5 and 100 nm, and the internal diameter of the pores present on the other layer of biocompatible polymer is between 200 and 1000 nm.

* * * * *